United States Patent [19]

Langbein et al.

[11] 4,010,164
[45] Mar. 1, 1977

[54] N-(FURYL-METHYL)-2-HYDROXY-5,9,9-TRIMETHYL-BENZOMORPHANS AND SALTS THEREOF

[75] Inventors: Adolf Langbein; Herbert Merz; Gerhard Walther; Klaus Stockhaus, all of Ingelheim, Rhine, Germany

[73] Assignee: Boehringer Ingelheim GmbH, Ingelheim, Rhine, Germany

[22] Filed: July 28, 1975

[21] Appl. No.: 599,427

Related U.S. Application Data

[63] Continuation-in-part of Ser. No. 454,964, March 27, 1974, abandoned.

[30] Foreign Application Priority Data

Mar. 28, 1973 Germany ......................... 2315339

[52] U.S. Cl. .................. 260/293.54; 260/DIG. 13; 424/267
[51] Int. Cl.² ........................................ C07D 405/06
[58] Field of Search ............... 260/293.54, DIG. 13

[56] References Cited

UNITED STATES PATENTS 2,924,603  2/1960  Gordon ........................ 260/293.54
3,764,606  10/1973  Akkerman et al. ........... 260/293.54
3,823,150  7/1974  Merz et al. .................... 260/293.54

*Primary Examiner*—Henry R. Jiles
*Assistant Examiner*—Robert T. Bond
*Attorney, Agent, or Firm*—Hammond & Littell

[57] ABSTRACT

Compounds of the formula

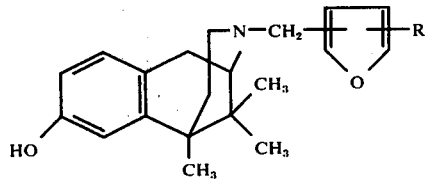

wherein R is hydrogen or methyl, and non-toxic, pharmacologically acceptable acid addition salts thereof; the compounds as well as their salts are useful as morphine-antagonists and analgesics.

7 Claims, No Drawings

N-(FURYL-METHYL)-2-HYDROXY-5,9,9-TRIMETHYL-BENZOMORPHANS AND SALTS THEREOF

This is a continuation-in-part of copending application Ser. No. 454,964 filed Mar. 27, 1974 now abandoned.

This invention relates to novel N-(furyl-methyl)-2'-hydroxy-5,9,9-trimethyl-benzomorphans and non-toxic acid addition salts thereof, as well as to methods of preparing these compounds.

More particularly, the present invention relates to a novel class of N-(furyl-methyl)-2'-hydroxy-5,9,9-trimethylbenzomorphans represented by the formula

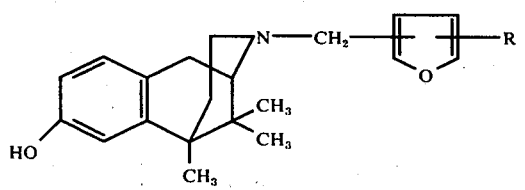

wherein R is hydrogen or methyl, and non-toxic, pharmacologically acceptable acid addition salts thereof.

These compounds occur as optically inactive racemates or racemic mixtures, as well as optical antipodes, and the present invention includes the optically inactive as well as the optically active forms of these compounds.

The benzomorphan derivatives embraced by formula I may be prepared by the following methods:

Method A

By reacting 2'-hydroxy-5,9,9-trimethyl-norbenzomorphan of the formula

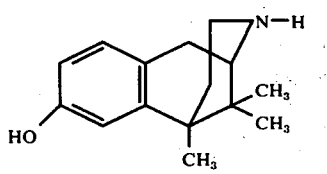

with a furylmethyl derivative of the formula

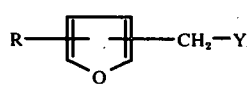

wherein R has the same meanings as in formula I, and Y is halogen, preferably chlorine or bromine, alkylsulfonyloxy or arylsulfonyloxy.

The reaction is advantageously performed in the presence of an acid-binding agent and of an inert solvent medium, by providing the calculated amount of the alkylating agent of the formula III or a slight excess thereover. Examples of suitable acid-binding agents are tertiary amines, such as triethylamine or N,N-dicyclohexyl-ethylamine; alkali metal carbonates, such as sodium carbonate or potassium carbonate; alkali metal bicarbonates, preferably sodium bicarbonate; alkali metal hydroxides; or alkali metal oxides. Examples of suitable inert solvent media are tetrahydrofuran, dioxane, methylene chloride, dimethylformamide, dimethylsulfoxide or mixtures of any two or more of these, preferred are mixtures of tetrahydrofuran and dimethylformamide. The reaction temperature is variable within wide limits, but the preferred reaction temperature range is from 0° C to the boiling point of the particular solvent medium which is used.

After completion of the reaction, the desired end product is isolated, purified and crystallized by conventional methods.

Method B

By reducing a 2'-oxy-5,9,9-trimethyl norbenzomorphan amide of the formula

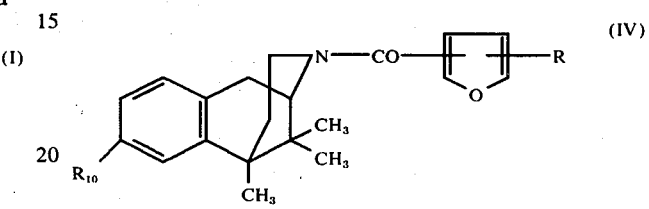

wherein R has the same meanings as in formula I, and $R_1$ is hydrogen or acyl, with a complex metal hydride, preferably lithium aluminum hydride.

The reduction is effected by using the calculated amount or advantageously an excess, preferably twice the calculated amount, of the complex metal hydride. The reaction is carried out in the presence of an inert solvent medium, such as an ether, preferably tetrahydrofurna. The reaction temperature may be varied within wide limits, but the preferred temperature range is, as in method A, between 0° C and the boiling point of the solvent medium.

When the complex metal hydride reduction is applied to an O-acyl-benzomorphanamide, i.e. a compound of the formula IV wherein $R_1$ is acyl, especially lower alkanoyl, the acyl substituent is split off simultaneously with the reduction of the carbonyl group, resulting in the formation of a compound of the formula I.

The desired end product may be isolated, purified and crystallized by conventional methods.

The starting compound of the formula II for method A is described in German Offenlegungsschrift No. 2,027,077.

The compounds of the formula III wherein Y is halogen may be prepared by reducing a corresponding known furancarboxylic acid ester to form a hydroxymethyl-furan, which may subsequently be converted into the corresponding halomethyl-furan with the aid of an acid halide by conventional procedures. Compounds of the formula III wherein Y is alkylsulfonyloxy or arylsulfonyloxy may be prepared analogously by esterifying a corresponding hydroxy-methyl-furan with the desired sulfonic acid.

The starting compounds of the formula IV may be prepared by reacting the norbenzomorphan of the formula II with a furan-carboxylic acid chloride of the formula

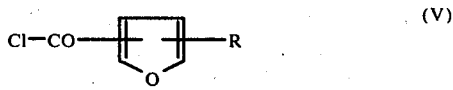

wherein R has the meanings previously defined.

A compound of the formula V, in turn, may be obtained by reacting a corresponding furan-carboxylic acid with an inorganic acid chloride, such as phosphorus pentachloride, phosphorus oxychloride or thionyl chloride.

The compounds embraced by formula I are organic bases and therefore form acid addition salts with inorganic or organic acids. Examples of non-toxic, pharmacologically acceptable acid addition salts are those formed with hydrochloric acid, hydrobromic acid, hydroiodic acid, acetic acid, propionic acid, butyric acid, valeric acid, hydrofluoric acid, sulfuric acid, phosphoric acid, nitric acid, pivalic acid, caproic acid, capric acid, oxalic acid, malonic acid, succinic acid, maleic acid, fumaric acid, lactic acid, tartaric acid, citric acid, benzoic acid, p-hydroxy-benzoic acid, phthalic acid, cinnamic acid, salicylic acid, ascorbic acid, 8-chlorotheophylline, methanesulfonic acid or the like. Such acid addition salts are obtained in conventional manner, i.e. dissolving the free base in an alcohol or ketone, and adding an ethereal solution of the desired acid.

The following examples illustrate the present invention and will enable others skilled in the art to understand it more completely. It should be understood, however, that the invention is not limited solely to the particular examples given below.

EXAMPLE 1

N-Furfuryl-2'-hydroxy-5,9,9-trimethyl-6,7-benzomorphan and its hydrochloride by method B 2.31 gm (0.01 mol) of 2'-hydroxy-5,9,9-trimethyl-benzomorphan were dissolved in 30 ml of absolute methylene chloride, 4 ml of triethylamine were added to the solution, and then 1.44 gm (0.011 mol) of 2-furan-carboxylic acid chloride were added dropwise over a period of 15 minutes at room temperature. The reaction mixture was then refluxed for one hour, subsequently diluted with methylene chloride, and then repeatedly vigorously shaken with water. The organic phase was dried with sodium sulfate, evaporated, the residue was dissolved in 35 ml of absolute tetrahydrofuran, and the resulting solution was added dropwise at room temperature to a solution of 0.76 gm (0.02 mol) of lithium aluminum hydride in 35 ml of absolute tetrahydrofuran. The reaction mixture was then refluxed for two hours, allowed to cool, and subsequently carefully admixed with 76 ml of an aqueous saturated solution of diammonium tartrate. The resulting mixture was allowed to stand at room temperature for a long period of time, whereupon the aqueous phase was separated from the tetrahydrofuran phase. The aqueous phase was extracted twice with 100 ml of methylene chloride each, and the extracts were combined and added to the tetrahydrofuran phase. The combined organic solutions were vigorously washed with water, dried over sodium sulfate and evaporated. The oily residue, the free base N-furfuryl-2'-hydroxy-5,9,9-trimethyl-6,7-benzomorphan, was dissolved in 20 ml of absolute ethanol, and the resulting solution was admixed with 5 ml of 2 N ethereal hydrochloric acid. Upon careful addition of ether to the acidic solution, a crystalline precipitate was formed which was collected by filtration, yielding 2.8 gm (80.6% of theory) of the hydrochloride of the formula

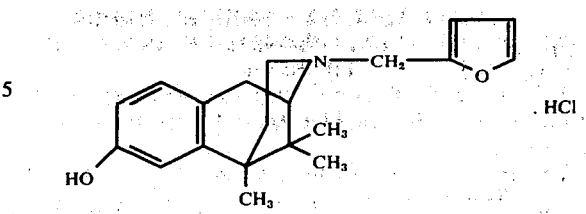

which had a melting point of 180°–184° C.

EXAMPLE 2

Using a procedure analogous to that described in Example 1, 69% of theory of N-(3-furyl-methyl)-2'-hydroxy-5,9,9-trimethyl-6,7-benzomorphan hydrochloride, m.p. 255°–258° C, was obtained from 2'-hydroxy-5,9,9-trimethyl-benzomorphan and 3-furan-carboxylic acid chloride.

EXAMPLE 3

Using a procedure analogous to that described in Example 1, 83.2% of theory of N-(2-methyl-3-furylmethyl)-2'-hydroxy-5,9,9-trimethyl-6,7-benzomorphan methanesulfonate, m.p. 214°–216° C, was obtained from 2'-hydroxy-5,9,9-trimethylbenzomorphan, 2-methyl-3-furan-carboxylic acid chlorine and methanesulfonic acid.

EXAMPLE 4

Using a procedure analogous to that described in Example 1, 55.4% of theory of N-(3-methyl-furfuryl)-2'-hydroxy-5,9,9-trimethyl-6,7-benzomorphan hydrochloride, m.p. 201°–204° C, was obtained from 2'-hydroxy-5,9,9-trimethyl-benzomorphan and 3-methyl-2-furan-carboxylic acid choride.

The compounds of the present invention, that is, the optically inactive as well as optically active forms of those embraced by formula I above and their non-toxic, pharmacologically acceptable acid addition salts, have useful morphineantagonistic and analgesic properties. More particularly, those compounds of this invention wherein R is hydrogen exhibit predominantly morphine-antagonistic activities, while those where R is methyl exhibit predominantly analgesic activities in warm-blooded animals, such as mice and rats.

The morphine-antagonistic properties were ascertained by means of the Haffner test [Deutsche Medizinische Wochenschrift 55, 731 (1929)], and the analgesic properties were ascertained by means of the hot-plate test [J. Pharmacol. Exp. Therap. 80, 300 (1944)] and the writhing test [ibid. 154, 319 (1966)].

For pharmaceutical purposes the compounds according to the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.16 to 5.0 mgm/kg body weight, preferably from 0.83 to 2.5 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

| | | |
|---|---:|---|
| N-Furfuryl-2'-hydroxy-5,9,9-trimethyl -6,7-benzomorphan hydrochloride | 50.0 | parts |
| Lactose | 95.0 | " |
| Corn starch | 45.0 | " |
| Colloidal silicic acid | 2.0 | " |
| Soluble starch | 5.0 | " |
| Magnesium stearate | 3.0 | " |
| Total | 200.0 | parts |

Preparation:

The benzomorphan compound is intimately admixed with the lactose and the corn starch, the mixture is moistened with an aqueous 10% solution of the soluble starch, the moist mass is forced through a 1 mm-mesh screen, the resulting granulate is dried at 40° C, the dry granulate is admixed with the colloidal silicic acid, and the composition is compressed into 200 mgm-tablets in a conventional tablet making machine. Each tablet contains 50 mgm of the benzomorphan compound and is an oral dosage unit composition with predominantly analgesic action.

| | | |
|---|---:|---|
| N-(3-Furylmethyl)-2'-hydroxy-5,9,9-trimethyl-6,7-benzomorphan hydrochloride | 75.0 | parts |
| Lactose | 100.0 | " |
| Corn starch | 65.0 | " |
| Colloidal silicic acid | 2.0 | " |
| Soluble starch | 5.0 | " |
| Magnesium stearate | 3.0 | " |
| Total | 250.0 | parts |

Preparation:

The ingredients are compounded in the same manner as in Example 5, and the composition is compressed into 250 mgm-pill cores which are subsequently coated with a thin shell consisting essentially of a mixture of sugar, talcum and gum arabic and finally polished with beeswax. Each coated pill contains 75 mgm of the benzomorphan compound and is an oral dosage unit composition with predominantly analgesic action.

| | | |
|---|---:|---|
| N-Furfuryl-2'-hydroxy-5,9,9-trimethyl-6,7-benzomorphan hydrochloride | 50.0 | parts |
| Lactose | 250.0 | " |
| Suppository base (e.g. cocoa butter) | 1400.0 | " |
| Total | 1700.0 | parts |

Preparation:

The benzomorphan compound is intimately admixed with the lactose, and the mixture is blended with the aid of an immersion homogenizer into the suppository base which had previously been melted and cooled to about 40° C. 1700 mgm-portions of the composition are poured into cooled suppository molds and allowed to harden therein. Each suppository contains 50 mgm of the benzomorphan compound and is a rectal dosage unit composition with predominantly analgesic action.

| | | |
|---|---:|---|
| N-(2-Methyl-3-furylmethyl)-2'-hydroxy-5,9,9-trimethyl-6,7-benzomorphan hydrochloride | 50.0 | parts |
| Sodium chloride | 5.0 | " |
| Double-distilled water q.s.ad | 5000.0 | " by vol. |

Preparation:

The benzomorphan compound and the sodium chloride are dissolved in the double-distilled water, the solution is filtered until free from suspended particles, and the filtrate is filled under aseptic conditions into 2 cc-ampules which are subsequently sterilized and sealed. Each ampule contains 50 mgm of the benzomorphan compound, and its contents are an injectable dosage unit composition with predominantly morphine-antagonistic action.

Analogous results are obtained when one of the other furylmethyl-substituted benzomorphans embraced by formula I or a non-toxic, pharmacologically acceptable acid addition salt is substituted for the particular benzomorphan salt in Examples 5 through 7; or when one of the other methylfurylmethyl-substituted benzomorphans embraced by formula I or a non-toxice, pharmacologically acceptable acid addition salt is substituted for the particular benzomorphan salt in Example 8. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. An optically inactive or optically active compound of the formula

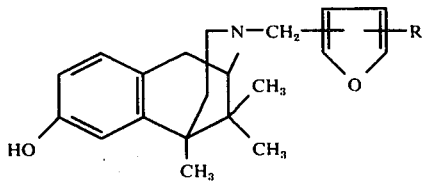

wherein R is hydrogen or methyl, or a non-toxic, pharmacologically acceptable acid addition salt thereof.

2. A compound of claim 1 where R is hydrogen, or a non-toxic, pharmacologically acceptable acid addition salt thereof.

3. A compound of claim 1 where R is methyl, or a non-toxic, pharmacologically acceptable acid addition salt thereof.

4. A compound of claim 2, which is N-furfuryl-2'-hydroxy-5,9,9-trimethyl-6,7-benzomorphan or a non-toxic, pharmacologically acceptable acid addition salt thereof.

5. A compound of claim 2, which is N-(3-furylmethyl)-2'-hydroxy-5,9,9-trimethyl-6,7-benzomorphan or a non-toxic, pharmacologically acceptable acid addition salt thereof.

6. A compound of claim 3, which is N-(2-methyl-3-furylmethyl)-2'-hydroxy-5,9,9-trimethyl-6,7-benzomorphan or a non-toxic, pharmacologically acceptable acid addition salt thereof.

7. A compound of claim 3, which is N-(3-methylfurfuryl)-2'-hydroxy-5,9,9-trimethyl-6,7-benzomorphan or a non-toxic, pharmacologically acceptable acid addition salt thereof.

* * * * *

UNITED STATES PATENT OFFICE
CERTIFICATE OF CORRECTION

Patent No. 4,010,164     Dated March 1, 1977

Inventor(s) ADOLF LANGBEIN, HERBERT MERZ, GERHARD WALTHER and KLAUS STOCKHAUS

It is certified that error appears in the above-identified patent and that said Letters Patent are hereby corrected as shown below:

Title:    "-METHYL)-2-HYDROXY" should read-- -METHYL)-2'-HYDROXY --

Column 2, first formula 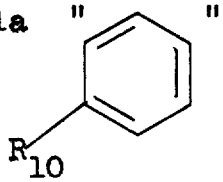 should read -- 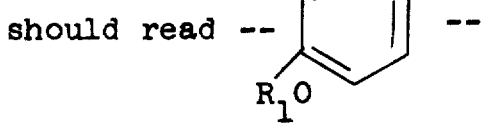 --

Column 2, lines 31-32 - "tetrahydrofurna" should read -- tetrahydrofuran --

"    5, after line 4- insert -- EXAMPLE 5

Tablets

The tablet composition is compounded from the following ingredients: --

"    5, after line 26 - insert -- EXAMPLE 6

Coated pills

The pill core composition is compounded from the following ingredients: --

UNITED STATES PATENT OFFICE
CERTIFICATE OF CORRECTION

Patent No. 4,010,164          Dated March 1, 1977

Inventor(s) ADOLF LANGBEIN, HERBERT MERZ, GERHARD WALTHER and KLAUS STOCKHAUS

It is certified that error appears in the above-identified patent and that said Letters Patent are hereby corrected as shown below:

Column 5, after line 45 - insert -- EXAMPLE 7

Suppositories

The suppository composition is compounded from the following ingredients: --

" 5, after line 63 - insert -- EXAMPLE 8

Hypodermic solution

The solution is compounded from the following ingredients: --

" 6, line 16       "non-toxice" should read -- non-toxic --

Signed and Sealed this

Twenty-first Day of June 1977

[SEAL]

Attest:

RUTH C. MASON
Attesting Officer

C. MARSHALL DANN
Commissioner of Patents and Trademarks